(12) United States Patent
Kim

(10) Patent No.: US 9,884,081 B2
(45) Date of Patent: Feb. 6, 2018

(54) ODOR AND SMELL FREE COMPOSITION FOR MOXIBUSTION AND METHOD OF MAKING THE SAME

(71) Applicant: Youngsu Kim, Centerville, VA (US)

(72) Inventor: Youngsu Kim, Centerville, VA (US)

(*) Notice: Subject to any disclaimer, the term of this patent is extended or adjusted under 35 U.S.C. 154(b) by 146 days.

(21) Appl. No.: 14/974,839

(22) Filed: Dec. 18, 2015

(65) Prior Publication Data

US 2017/0173096 A1  Jun. 22, 2017

(51) Int. Cl.
| | | |
|---|---|---|
| *A61K 36/00* | (2006.01) |
| *A61K 36/282* | (2006.01) |
| *A61K 33/00* | (2006.01) |
| *A61K 33/24* | (2006.01) |

(52) U.S. Cl.
CPC ............ *A61K 36/282* (2013.01); *A61K 33/00* (2013.01); *A61K 33/24* (2013.01)

(58) Field of Classification Search
CPC .................................................... A61K 36/00
See application file for complete search history.

(56) References Cited

U.S. PATENT DOCUMENTS 7,595,066 B2   9/2009   Kim

FOREIGN PATENT DOCUMENTS

| CN | 102672782 A | * | 9/2012 |
| WO | 2010/018911 A1 | | 2/2010 |

* cited by examiner

*Primary Examiner* — Qiuwen Mi
(74) *Attorney, Agent, or Firm* — Novick, Kim & Lee, PLLC; Jae Youn Kim

(57) ABSTRACT

Provided is a composition having moxibustion effects and a formulation acceptable in oriental medicine. More particularly, the composition has moxibustion effects without odor commonly associated with moxibustion.

10 Claims, No Drawings

ODOR AND SMELL FREE COMPOSITION FOR MOXIBUSTION AND METHOD OF MAKING THE SAME

TECHNICAL FIELD

The present invention relates to a composition having moxibustion effects and a method of producing the same. More particularly, the present invention relates to a composition having moxibustion effects without odor commonly associated with moxibustion and a method of producing the same.

BACKGROUND ART

Oriental medicine, also known as Chinese Traditional Medicine (CTM), has been established through clinical tests for thousands of years. In an aspect of CTM, stimulation is applied to acupoints of meridians to treat specific diseases and to improve general health. Therapeutic effects are achieved by stimulating smooth circulation of blood and chi throughout the body.

Representative examples of such stimulation treatments include acupuncture and thermal application of herbal compositions to the skin. Such herbal compositions often include *Artemisia* species, e.g., moxa, as an active ingredient and the thermal application is thus referred to as moxibustion. Conventional moxibustion is performed by burning *artemisia* and/or various herbal blends on the skin or on acupoints, and the therapeutic effects of moxibustion is produced by the active ingredients and the heat released when the herbal compositions are burned.

However, there exist dangers of environmental pollution due to smoke released when moxa is burned. More particularly, burning moxa creates a distinct odor much like the odor produced when burning a marijuana plant. Because of this distinct odor, patients who receive moxibustion treatment may be misunderstood if the treatment is performed in public or if they enter a public area after moxibustion treatment. For these reasons, people are unwilling to receive moxibustion treatment despite its various benefits, which makes moxibustion difficult to popularize and globalize.

Provided therefore, is a composition having moxibustion effects which significantly reduces or eliminates odor relative to traditional moxibustion compositions.

SUMMARY OF THE INVENTION

In accordance with one aspect of the present invention, provided is a composition having moxibustion effects, the composition including moxa, far-infrared radiating powder, and baking soda at 1:1:10 ratio by weight %.

In another embodiment of the present invention, provided is a composition having moxibustion effects, the composition including, by weight, 75-80% of moxa, 10-12% of far-infrared radiating powder, and 10-12% of baking soda.

In another embodiment of the present invention, provided is a composition having moxibustion effects, the composition including, by weight, 70-80% of moxa, 5-7% baking soda, 5-7% of elvan stone powder, and 5-7% germanium powder.

When thermally applied in moxibustion, the embodiments of the present invention removes or significantly decreases the marijuana-like odor produced in traditional moxibustion treatments while retaining the therapeutic effects of moxibustion.

In accordance with another aspect of the present invention, provided is a method for preparing a composition having moxibustion effects, the method including the steps of: preparing moxa by obtaining *artemisia* plant, drying the *artemisia* plant, and shredding and/or pulverizing the dried *artemisia* plant; and mixing the prepared moxa with far-infrared radiating powder and baking soda at 1:1:10 ratio by weight %.

In another embodiment, the prepared moxa is mixed with far-infrared radiating powder and baking soda at 75-80%, 10-12%, and 10-12%, by weight, respectively, in the mixing step.

In another embodiment of the present invention, provided is a method for preparing a composition having moxibustion effects, the method including the steps of: preparing moxa by obtaining *artemisia* plant, shredding and/or pulverizing the *artemisia* plant, and drying the shredded and/or pulverized *artemisia* plant; and mixing the prepared moxa with elvan stone powder, baking soda, and germanium powder at 70-80%, 5-7%, 5-7%, and 5-7%, by weight, respectively.

In another embodiment, the *artemisia* plant is dried for at least a period of three years in the moxa preparing step.

These and/or other aspects will become apparent and more readily appreciated from the following description of embodiments of the present invention.

DETAILED DESCRIPTION

It should be understood that the exemplary embodiments described therein should be considered in a descriptive sense only and not for purposes of limitation. Descriptions of features or aspects within each embodiment should typically be considered as available for other similar features or aspects in other embodiments.

In accordance with one aspect of the present invention, provided is a composition having moxibustion effects. The composition includes moxa, far-infrared radiating powder, and baking soda at 1:1:10 ratio by weight %.

In another embodiment of the present invention, provided is a composition having moxibustion effects, the composition including, by weight, 75-80% of moxa, 10-12% of far-infrared radiating powder, and 10-12% of baking soda.

In yet another embodiment of the present invention, provided is a composition having moxibustion effects, the composition including, by weight, 70-80% of moxa, 5-7% baking soda, 5-7% of elvan stone powder, and 5-7% germanium powder.

The composition may also have additional herbal mixtures and resin, as known and available in the art of oriental medicine.

Moxa is well known in the art of oriental medicine as having therapeutic effects through thermal application, or moxibustion, and the method of its preparation is also well-known. Moxa may be prepared from mugroot (*Artemisia argyi*), in which mugroot is obtained, dried, shredded and/or pulverized in accordance with preparation procedure well-known in the art. Alternative preparation procedures available to those of ordinary skill in the art of oriental medicine may also be used.

Moxa may include other species of *Artemisia* acceptable in oriental medicine, such as but not limited to, *Artemisia* spp., *Artemisia annua* L., *Artemisia asiatica*, *Artemisia vulgaris* L., *Artemisia capillaris*, *Artemisia princeps* Pamp., etc. *Artemisia* species growing naturally in Korea are preferred. The *Artemisia* species can be used independently or in combination with one another. That is, a composition having moxibustion effects according to the present invention may comprise one or more species of *Artemisia*.

Far-infrared radiating powder used in the composition of the present invention may be, but is not limited to, bioceramics, tourmaline, kiyoseki, quartz-porphyry, illite, biotite, germanium, monazite, and elvan stone. Far-infrared radiating powders capable of anion emission effects are preferred. Particularly, elvan stone ("maek ban seok" in Korean), which comprises mainly of $SiO_2$ and $Al_2O_3$, and has strong adsorption and ion exchange properties, is preferred.

For far-infrared radiating powder, a ratio of 12% or less by weight is preferred because if the ratio is greater than 12%, the composition may not burn properly during moxibustion.

Baking soda, or sodium bicarbonate ($NaHCO_3$), is a chemical compound readily available to the public for household uses. It is a white solid which often appears as fine powder.

By mixing moxa, far-infrared radiating powder, and baking soda, the resulting composition having moxibustion effect produces significantly less or no odor when thermally applied in moxibustion treatment. Specifically, the odor which resembles that of burned marijuana is significantly reduced or eliminated.

The present moxa composition can be made by preparing moxa, or alternative *artemisia* species acceptable in oriental medicine, by obtaining *artemisia* plant, cutting and pulverizing the *artemisia* plant, and drying the cut and pulverized *artemisia* plant. It is preferable that the cut and pulverized *artemisia* plant should be dried for at least a period of three years. The dried moxa or *artemisia* can be mixed with far-infrared radiating powder and baking soda by any manner available in the art.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A composition for moxibustion, comprising:
   moxa, or acceptable alternative *artemisia* species;
   far-infrared radiating powder; and
   baking soda,
   wherein the moxibustion is odorless when used in thermal treatment.

2. The composition of claim 1, wherein the moxa, far-infrared radiating powder, and baking soda have ratio of 1:1:10 by weight %.

3. The composition of claim 1, wherein
   the moxa, or acceptable alternative *artemisia* species, has a ratio of 75-80% by weight,
   the far-infrared radiating powder has a ratio of 10-12% by weight, and
   the baking soda has a ratio of 10-12% by weight.

4. The composition of claim 3, wherein the far-infrared powder is one of elvan stone powder or germanium powder.

5. The composition of claim 1, wherein the far-infrared radiation podwer includes elvan stone powder and germanium powder.

6. The composition of claim 5, wherein:
   the moxa, or acceptable alternative *artemisia* species, has a ratio of 70-80% by weight,
   the elvan stone powder has a ratio of 5-7% by weight,
   the baking soda has a ratio of 5-7% by weight, and
   the germanium powder has a ratio of 5-7% by weight.

7. A method of preparing a composition for moxibustion, comprising
   preparing moxa, or alternative *artemisia* species acceptable in oriental medicine, by obtaining *artemisia* plant, cutting and pulverizing the *artemisia* plant, and drying the cut and pulverized *artemisia* plant; and
   mixing the prepared moxa with far-infrared radiating powder and baking soda,
   wherein the moxibustion is odorless when used in thermal treatment.

8. The method of claim 7, wherein the moxa, far-infrared radiating powder, and baking soda are mixed at 75-80%, 10-12%, and 10-12%, by weight, respectively.

9. The method of preparing a composition for moxibustion of claim 7, wherein the far-infrared radiating powder includes elvan stone powder and germanium powder.

10. The method of claim 9, wherein the moxa, elvan stone powder, baking soda, and germanium powder are mixed at 70-80%, 5-7%, 5-7%, and 5-7%, by weight, respectively.

* * * * *